(12) United States Patent
Xu

(10) Patent No.: US 6,242,014 B1
(45) Date of Patent: Jun. 5, 2001

(54) METHODS FOR USING PECTATE LYASES IN BAKING

(75) Inventor: Feng Xu, Woodland, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/395,858

(22) Filed: Sep. 14, 1999

Related U.S. Application Data

(63) Continuation-in-part of application No. 09/156,298, filed on Sep. 17, 1998, now abandoned.
(51) Int. Cl.[7] .................................................. A21D 2/00
(52) U.S. Cl. .............................. 426/18; 426/19; 426/20; 426/50; 426/52; 426/549
(58) Field of Search .................................. 426/18, 19, 20, 426/49, 50, 52, 27, 549

(56) References Cited

PUBLICATIONS

Zetelakine Horvath, AN 81(05):J0722 FSTA, abstracting Elelmezesi Ipar, 1980, 34(2) 72–76, 1980.*

* cited by examiner

*Primary Examiner*—Leslie Wong
(74) *Attorney, Agent, or Firm*—Robert L. Starnes

(57) ABSTRACT

The present invention relates to methods for preparing a dough, including incorporating into the dough an effective amount of one or more pectate lyases which improve one or more properties of the dough or a baked product obtained from the dough. The present invention also relates to methods for preparing a baked product. The present invention also relates to compositions including an effective amount of one or more pectate lyases for improving one or more properties of a dough and/or a baked product obtained from the dough. The present invention further relates to doughs or baked products and to pre-mixes for a dough.

24 Claims, No Drawings

SEQUENCE LISTING

<160> NUMBER OF SEQ ID NOS: 12

<210> SEQ ID NO: 1
<211> LENGTH: 1077
<212> TYPE: DNA
<213> ORGANISM: Bacillus agaradherens

<400> SEQUENCE: 1

```
atgactaaag tctttaaatt gttactggca ttagctctcg ttttaccagt tatctcattt      60
agttctcctg cctcgcaagc tgcttcaaat cagccaactt ctaacggacc acaaggctat     120
gcgtcaatga atggagggac aaccggtggt gcaggcggcc gtgtcgaata tgcaagcacc     180
ggagcgcaaa ttcagcaatt gatagataat cgcagccgaa gtaataaccc tgatgaacca     240
ttaacgattt atgtaaacgg aacgattaca caaggaaatt ccccacagtc ccttatagat     300
gttaaaaatc accgtggaaa agctcatgaa attaaaaaca tctctattat cggtgtagga     360
acaaatggag agtttgatgg cattgggata agactatcaa acgcccataa tatcattatc     420
caaaatgtat caattcatca tgtgcgagag ggagaaggca cggctattga agtgacagat     480
gagagtaaaa acgtgtggat cgatcacaac gagttttata gtgaatttcc aggtaatgga     540
gactcagatt attacgatgg tctcgtagac ataaaaagaa acgctgaata tattacggtt     600
tcatggaata gtttgagaa tcattggaaa acgatgctcg tcggtcatac tgataatgcc     660
tcattagcgc cagataaaat tacgtaccat cacaattatt ttaataatct taattcacgt     720
gtcccgctta ttcgatacgc tgatgttcca atgttcaata actattttaa agacattaac     780
gatacagcga ttaacagtcg tgtaggggcc cgtgtctttg tagaaaacaa ctatttgac     840
aacgtaggat caggacaagc tgacccaacg actggtttta ttaaagggcc tgttggttgg     900
ttctatggaa gtccgagtac tggatattgg aatttacgtg gaaatgtatt tgttaataca     960
ccgaatagtc atttaagctc tacaacaaac tttacaccac catatagtta caaagtccaa    1020
tcagctaccc aagctaagtc gtcggttgaa caacattcgg gagtaggtgt tatcaac      1077
```

<210> SEQ ID NO: 2
<211> LENGTH: 359
<212> TYPE: PRT
<213> ORGANISM: Bacillus agaradherens

<400> SEQUENCE: 2

```
Met Thr Lys Val Phe Lys Leu Leu Leu Ala Leu Ala Leu Val Leu Pro
  1               5                  10                  15

Val Ile Ser Phe Ser Ser Pro Ala Ser Gln Ala Ala Ser Asn Gln Pro
             20                  25                  30

Thr Ser Asn Gly Pro Gln Gly Tyr Ala Ser Met Asn Gly Gly Thr Thr
         35                  40                  45

Gly Gly Ala Gly Gly Arg Val Glu Tyr Ala Ser Thr Gly Ala Gln Ile
     50                  55                  60

Gln Gln Leu Ile Asp Asn Arg Ser Arg Ser Asn Asn Pro Asp Glu Pro
 65                  70                  75                  80

Leu Thr Ile Tyr Val Asn Gly Thr Ile Thr Gln Gly Asn Ser Pro Gln
                 85                  90                  95

Ser Leu Ile Asp Val Lys Asn His Arg Gly Lys Ala His Glu Ile Lys
            100                 105                 110

Asn Ile Ser Ile Ile Gly Val Gly Thr Asn Gly Glu Phe Asp Gly Ile
        115                 120                 125
```

```
Gly Ile Arg Leu Ser Asn Ala His Asn Ile Ile Gln Asn Val Ser
    130                 135                 140

Ile His His Val Arg Glu Gly Glu Thr Ala Ile Glu Val Thr Asp
145                 150                 155                 160

Glu Ser Lys Asn Val Trp Ile Asp His Asn Glu Phe Tyr Ser Glu Phe
                165                 170                 175

Pro Gly Asn Gly Asp Ser Asp Tyr Tyr Asp Gly Leu Val Asp Ile Lys
                180                 185                 190

Arg Asn Ala Glu Tyr Ile Thr Val Ser Trp Asn Lys Phe Glu Asn His
                195                 200                 205

Trp Lys Thr Met Leu Val Gly His Thr Asp Asn Ala Ser Leu Ala Pro
    210                 215                 220

Asp Lys Ile Thr Tyr His His Asn Tyr Phe Asn Asn Leu Asn Ser Arg
225                 230                 235                 240

Val Pro Leu Ile Arg Tyr Ala Asp Val His Met Phe Asn Asn Tyr Phe
                245                 250                 255

Lys Asp Ile Asn Asp Thr Ala Ile Asn Ser Arg Val Gly Ala Arg Val
                260                 265                 270

Phe Val Glu Asn Asn Tyr Phe Asp Asn Val Gly Ser Gly Gln Ala Asp
                275                 280                 285

Pro Thr Thr Gly Phe Ile Lys Gly Pro Val Gly Trp Phe Tyr Gly Ser
    290                 295                 300

Pro Ser Thr Gly Tyr Trp Asn Leu Arg Gly Asn Val Phe Val Asn Thr
305                 310                 315                 320

Pro Asn Ser His Leu Ser Ser Thr Thr Asn Phe Thr Pro Pro Tyr Ser
                325                 330                 335

Tyr Lys Val Gln Ser Ala Thr Gln Ala Lys Ser Ser Val Glu Gln His
                340                 345                 350

Ser Gly Val Gly Val Ile Asn
                355

<210> SEQ ID NO: 3
<211> LENGTH: 42
<212> TYPE: DNA
<213> ORGANISM: Bacillus subtilis

<400> SEQUENCE: 3
gtcgccgggg cggccgctat caattggtaa ctgtatctca gc                  42

<210> SEQ ID NO: 4
<211> LENGTH: 64
<212> TYPE: DNA
<213> ORGANISM: Bacillus subtilis

<400> SEQUENCE: 4
gtcgcccggg agctctgatc aggtaccaag cttgtcgacc tgcagaatga ggcagcaaga  60
agat                                                              64

<210> SEQ ID NO: 5
<211> LENGTH: 61
<212> TYPE: DNA
<213> ORGANISM: Bacillus subtilis

<400> SEQUENCE: 5
gtcggcggcc gctgatcacg taccaagctt gtcgacctgc agaatgaggc agcaagaaga  60
t                                                                 61
```

<210> SEQ ID NO: 6
<211> LENGTH: 35
<212> TYPE: DNA
<213> ORGANISM: Bacillus subtilis

<400> SEQUENCE: 6
gtcggagctc tatcaattgg taactgtatc tcagc                      35

<210> SEQ ID NO: 7
<211> LENGTH: 35
<212> TYPE: DNA
<213> ORGANISM: Bacillus subtilis

<400> SEQUENCE: 7
aacagctgat cacgactgat cttttagctt ggcac                      35

<210> SEQ ID NO: 8
<211> LENGTH: 37
<212> TYPE: DNA
<213> ORGANISM: Bacillus subtilis

<400> SEQUENCE: 8
aactgcagcc gcggcacatc ataatgggac aaatggg                    37

<210> SEQ ID NO: 9
<211> LENGTH: 39
<212> TYPE: DNA
<213> ORGANISM: Bacillus liceniformis

<400> SEQUENCE: 9
ctaactgcag ccgcggcagc ttctgcctta aactcgggc                  39

<210> SEQ ID NO: 10
<211> LENGTH: 42
<212> TYPE: DNA
<213> ORGANISM: Bacillus liceniformis

<400> SEQUENCE: 10
gcgttgagac gcgcggccgc tgaatgcccc ggacgtttca cc              42

<210> SEQ ID NO: 11
<211> LENGTH: 1026
<212> TYPE: DNA
<213> ORGANISM: Bacillus liceniformis

<400> SEQUENCE: 11
atgaagaaat taatcagcat catctttatc tttgtattag gggttgtcgg gtcattgaca      60
gcggcggttt cggcagaagc agcttctgcc ttaaactcgg gcaaagtaaa tccgcttgcc     120
gacttcagct taaaaggctt tgccgcacta acggcggaa caacgggcgg agaaggcggt     180
cagacggtaa ccgtaacaac gggagatcag ctgattgcgg cattaaaaaa taagaatgca     240
aatacgcctt taaaaattta tgtcaacggc accattacaa catcaaatac atccgcatca     300
aagattgacg tcaaagacgt gtcaaacgta tcgattgtcg gatcagggac caaaggggaa     360
ctcaaaggga tcggcatcaa atatggcgg gccaacaaca tcatcatccg caacttgaaa     420
attcacgagg tcgcctcagg cgataaagac gcgatcggca ttgaaggccc ttctaaaaac     480 atttggttg atcataatga gctttaccac agcctgaacg ttgacaaaga ttactatgac     540
ggattatttg acgtcaaaag agatgcggaa tatattacat tctcttggaa ctatgtgcac     600

```
gatggatgga aatcaatgct gatgggttca tcggacagcg ataattacaa caggacgatt   660
acattccatc ataactggtt tgagaatctg aattcgcgtg tgccgtcatt ccgtttcgga   720
gaaggccata tttacaacaa ctatttcaat aaaatcatcg acagcggaat taattcgagg   780
atgggcgcgc gcatcagaat tgagaacaac ctctttgaaa acgccaaaga tccgattgtc   840
tcttggtaca gcagttcacc gggctattgg catgtatcca acaacaaatt tgtaaactct   900 agggcagta tgccgactac ctctactaca acctataatc cgccatacag ctactcactc   960
gacaatgtcg acaatgtaaa atcaatcgtc aagcaaaatg ccggagtcgg caaaatcaat  1020
ccataa                                                              1026
```

<210> SEQ ID NO: 12
<211> LENGTH: 341
<212> TYPE: PRT
<213> ORGANISM: Bacillus licheniformis

<400> SEQUENCE: 12

```
Met Lys Lys Leu Ile Ser Ile Ile Phe Ile Phe Val Leu Gly Val Val
 1               5                  10                  15

Gly Ser Leu Thr Ala Ala Val Ser Ala Glu Ala Ala Ser Ala Leu Asn
                20                  25                  30

Ser Gly Lys Val Asn Pro Leu Ala Asp Phe Ser Leu Lys Gly Phe Ala
            35                  40                  45

Ala Leu Asn Gly Gly Thr Thr Gly Gly Glu Gly Gln Thr Val Thr
        50                  55                  60

Val Thr Thr Gly Asp Gln Leu Ile Ala Ala Leu Lys Asn Lys Asn Ala
65                  70                  75                  80

Asn Thr Pro Leu Lys Ile Tyr Val Asn Gly Thr Ile Thr Ser Asn
                85                  90                  95

Thr Ser Ala Ser Lys Ile Asp Val Lys Asp Val Ser Asn Val Ser Ile
            100                 105                 110

Val Gly Ser Gly Thr Lys Gly Glu Leu Lys Gly Ile Gly Ile Lys Ile
        115                 120                 125

Trp Arg Ala Asn Asn Ile Ile Ile Arg Asn Leu Lys Ile His Glu Val
    130                 135                 140

Ala Ser Gly Asp Lys Asp Ala Ile Gly Ile Glu Gly Pro Ser Lys Asn
145                 150                 155                 160

Ile Trp Val Asp His Asn Glu Leu Tyr His Ser Leu Asn Val Asp Lys
                165                 170                 175

Asp Tyr Tyr Asp Gly Leu Phe Asp Val Lys Arg Asp Ala Glu Tyr Ile
            180                 185                 190

Thr Phe Ser Trp Asn Tyr Val His Asp Gly Trp Lys Ser Met Leu Met
        195                 200                 205

Gly Ser Ser Asp Ser Asp Asn Tyr Asn Arg Thr Ile Thr Phe His His
    210                 215                 220

Asn Trp Phe Glu Asn Leu Asn Ser Arg Val Pro Ser Phe Arg Phe Gly
225                 230                 235                 240

Glu Gly His Ile Tyr Asn Asn Tyr Phe Asn Lys Ile Ile Asp Ser Gly
                245                 250                 255

Ile Asn Ser Arg Met Gly Ala Arg Ile Arg Ile Glu Asn Asn Leu Phe
            260                 265                 270

Glu Asn Ala Lys Asp Pro Ile Val Ser Trp Tyr Ser Ser Pro Gly
        275                 280                 285

Tyr Trp His Val Ser Asn Asn Lys Phe Val Asn Ser Arg Gly Ser Met
```

```
              290                 295                 300

Pro Thr Thr Ser Thr Thr Thr Tyr Asn Pro Pro Tyr Ser Tyr Ser Leu
305                 310                 315                 320

Asp Asn Val Asp Asn Val Lys Ser Ile Val Lys Gln Asn Ala Gly Val
            325                 330                 335

Gly Lys Ile Asn Pro
            340
```

METHODS FOR USING PECTATE LYASES IN BAKING

CROSS-REFERENCE TO RELATED APPLICATION

This application is a continuation-in-part of U.S. application Ser. No. 09/156,298 filed on Sep. 17, 1998, now abandoned, which application is fully incorporated herein by reference.

BACKGROUND OF THE INVENTION

1. Field of the Invention

The present invention relates to methods for preparing a dough and/or baked product with a pectate lyase.

2. Description of the Related Art

The strength of a dough is an important aspect of baking for both small-scale and large-scale applications, whereas a weak dough is less tolerant to these treatments. A strong dough has a greater tolerance of mixing time, proofing time, and mechanical vibrations during dough transport than a weak dough. A strong dough with superior rheological and handling properties results from flour containing a strong gluten network. Flour with a low protein content or a poor gluten quality results in a weak dough.

Dough "conditioners" are well known in the baking industry. The addition of conditioners to bread dough has resulted in improved machinability of the dough and improved texture, volume, flavor, and freshness (anti-staling) of the bread. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough. However, the use of several of the currently available chemical oxidizing agents has been met with consumer resistance or is not permitted by regulatory agencies.

The use of enzymes as dough conditioners has been considered as an alternative to the chemical conditioners. A number of enzymes have been used recently as dough and/or bread improving agents, in particular, enzymes that act on components present in large amounts in the dough. Examples of such enzymes are found within the groups of amylases, proteases, glucose oxidases, and (hemi)cellulases, including pentosanases.

It is the object of the present invention to improve the properties of dough and/or baked products by the use of a pectate lyase.

SUMMARY OF THE INVENTION

The present invention relates to methods for preparing a dough, comprising incorporating into the dough an effective amount of one or more pectate lyases.

The present invention also relates to methods for preparing a baked product.

The present invention also relates to compositions comprising an effective amount of one or more pectate lyases, for improving one or more properties of a dough and/or a baked product obtained from the dough, and a carrier and/or a baking ingredient.

The present invention also relates to doughs or baked products.

The present invention further relates to pre-mixes for a dough comprising an effective amount of one or more pectate lyases, for improving one or more properties of a dough and/or a baked product obtained from the dough, and a carrier and/or a baking ingredient.

DETAILED DESCRIPTION OF THE INVENTION

The present invention relates to methods for preparing a dough and/or a baked product comprising incorporating into the dough an effective amount of one or more pectate lyases, which improve one or more properties of the dough and/or the baked product obtained from the dough relative to a dough or a baked product in which a pectate lyase is not incorporated.

The phrase "incorporating into the dough" is defined herein as adding the pectate lyase(s) to the dough, any ingredient from which the dough is to be made, and/or any mixture of dough ingredients from which the dough is to be made. In other words, the pectate lyase(s) may be added in any step of the dough preparation and may be added in one, two, or more steps.

The term "effective amount" is defined herein as an amount of a pectate lyase that is sufficient for providing a measurable effect on at least one property of interest of the dough and/or baked product.

The term "improved property" is defined herein as any property of a dough and/or a product obtained from the dough, particularly a baked product, which is improved by the action of a pectate lyase relative to a dough or product in which a pectate lyase is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The use of a pectate lyase may result in an increased strength, stability, and/or reduced stickiness of the dough, resulting in improved machinability, as well as in an increased volume and improved crumb structure and softness of the baked product. The effect on the dough may be particularly advantageous when a poor quality flour is used. Improved machinability is of particular importance in connection with dough that is to be processed industrially.

The improved property may be determined by comparison of a dough and/or a baked product prepared with and without addition of one or more pectate lyases in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g, TAXT2) as known in the art.

The term "improved flavor of the baked product" is evaluated as mentioned above by a trained test panel.

The term "improved antistaling of the baked product" is defined herein as the properties of a baked product that have a reduced rate of deterioration of quality parameters, e.g., softness and/or elasticity, during storage.

In a preferred embodiment, the one or more pectate lyases improve one or more properties of the dough or the baked product obtained from the dough. In another preferred embodiment, the one or more pectate lyases improve one or more properties of the dough and the baked product obtained from the dough.

In a preferred embodiment, the improved property is increased strength of the dough. In another preferred embodiment, the improved property is increased elasticity of the dough. In another preferred embodiment, the improved property is increased stability of the dough. In another preferred embodiment, the improved property is reduced stickiness of the dough. In another preferred embodiment, the improved property is improved extensibility of the dough. In another preferred embodiment, the improved property is improved machinability of the dough. In another preferred embodiment, the improved property is increased volume of the baked product. In another preferred embodiment, the improved property is improved crumb structure of the baked product. In another preferred embodiment, the improved property is improved softness of the baked product. In another preferred embodiment, the improved property is improved flavor of the baked product. In another preferred embodiment, the improved property is improved antistaling of the baked product.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters*.

The term "baked product" is defined herein as any product prepared from a dough, either of a soft or a crisp character.

Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

The pectate lyase(s) may be any pectate lyase which provides an improved property to a dough and/or to a baked product obtained from the dough.

The term "pectate lyase" as used in the present invention is defined herein as a poly(1,4-alpha-D-galacturonide) lyase which eliminates Δ-4,5-D-galacturonate residues from pectate to yield oligosaccharides with 4-deoxy-alpha-D-gluc-4-enuronosyl groups at their non-reducing ends, thus bringing about depolymerization. Pectate lyases are defined by the Nomenclature Committee of the International Union of Biochemistry on the Nomenclature and Classification of Enzymes and listed as enzyme subclass E.C. 4.2.2.2. A pectate lyase is also known as a polygalacturonic transeliminase, pectic acid transeliminase, polygalacturonate lyase, endopectin methyltranseliminase, pectate transeliminase, endogalacturonate transeliminase, pectic acid lyase, pectic lyase, polygalacturonic acid lyase, endo-alpha-1,4-polygalacturonic acid lyase, alpha-1,4-D-endopolygalacturonic acid lyase, PGA lyase, polygalacturonase, polygalacturonic acid trans-eliminase, pectin trans-eliminase, or pectin transeliminase.

In the methods of the present invention, any pectate lyase may be used which possesses suitable enzyme activity in a pH and temperature range appropriate for making a dough and/or a baked product. It is preferable that the pectate lyase(s) is active over broad pH and temperature ranges.

In a preferred embodiment, the pectate lyase(s) has a pH optimum in the range of about 3 to about 10. In a more preferred embodiment, the pectate lyase(s) has a pH optimum in the range of about 4.5 to about 8.5.

In another preferred embodiment, the pectate lyase(s) has a temperature optimum in the range of about 5° C. to about 100° C. In a more preferred embodiment, the pectate lyase(s) has a temperature optimum in the range of about 25° C. to about 75° C.

The source of a pectate lyase is not critical for improving one or more properties of a dough and/or a baked product. Accordingly, the pectate lyase(s) may be obtained from any source such as a plant, microorganism, or animal. The pectate lyase(s) is preferably obtained, e.g., from a microbial source, such as a bacterium or a fungus, e.g., a filamentous fungus or a yeast. See, for example, Nasser et al., 1993, *FEBS Letters* 335: 319–326); Kim et al., 1994, *Biosci. Biotech. Biochem.* 58: 947–949); Dave and Vaughn, 1971, *Journal of Bacteriology*. 108: 166–174); Nagel and Vaughn, 1961, *Archives of Biochemistry Biophysics* 93: 344–352; Karbassi and Vaughn, 1980, *Canadian Journal of Microbiol.* 26: 377–384); Hasegawa and Nagel, 1966, *Journal of Food Science* 31: 838–845; and Kelly and Fogarty, 1978, *Canadian Journal of Microbiology* 24:1164–1172.

In a preferred embodiment, the pectate lyase(s) is a bacterial pectate lyase. For example, the pectate lyase(s) may be an Acetobacter, Acinetobacter, Agrobacterium, Alcaligenes, Arthrobacter, Azotobacter, Bacillus, Comamonas, Clostridium, Erwinia, Gluconobacter, Halobacterium, Klebsiella, Mycobacterium, Rhizobium, Salmonella, Serratia, Streptomyces, *E. coli*, Pseudomonas, Wolinella, or Xanthomonas pectate lyase.

In a more preferred embodiment, the pectate lyase(s) is a *Bacillus agaradherens, Bacillus polymyxa, Bacillus*

*pumilus, Bacillus stearothermophilus, Bacillus subtilis, Clostridium felsineum, Clostridium thermocellum, Erwinia amylovora, Erwinia carotovora, Erwinia chrysanthemi, Klebsiella oxytoca, Pseudomonas marginalis, Pseudomonas putida, Pseudomonas syringae, Pseudomonas viridiflava, Streptomyces fradiae, Streptomyces nitrosporeus*, or *Xanthomonas campestris* pectate lyase.

In another preferred embodiment, the pectate lyase(s) is a fungal pectate lyase. For example, the pectate lyase(s) may be a yeast strain pectate lyase as a Candida, Kluyveromyces, Pichia, Saccharomyces, Schizosaccharomyces, or Yarrowia pectate lyase; or a filamentous fungal pectate lyase such as an Acremonium, Aspergillus, Aureobasidium, Chrysosporium, Cryptococcus, Filibasidium, Fusarium, Humicola, Magnaporthe, Monilia, Mucor, Myceliophthora, Neocallimastix, Neurospora, Paecilomyces, Penicillium, Phanerochaete, Piromyces, Rhizoctonia, Schizophyllum, Sclerotium, Sporotrichum, Talaromyces, Thermoascus, Thielavia, Tolypocladium, or Trichoderma pectate lyase.

In another more preferred embodiment, the pectate lyase(s) is a *Kluyveromyces marxianus, Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* pectate lyase.

In another more preferred embodiment, the pectate lyase(s) is an *Aspergillus aculeatus, Aspergillus awamori, Aspergillus foetidus, Aspergillus fumigatus, Aspergillus heteromorphus, Aspergillus japonicus, Aspergillus nidulans, Aspergillus niger, Aspergillus oryzae, Chrysosporium lignorum, Fusarium bactridioides, Fusarium cerealis, Fusarium crookwellense, Fusarium culmorum, Fusarium graminearum, Fusarium graminum, Fusarium heterosporum, Fusarium negundi, Fusarium moniliforme, Fusarium oxysporum, Fusarium reticulatum, Fusarium roseum, Fusarium sambucinum, Fusarium sarcochroum, Fusarium semitectum, Fusarium solani, Fusarium sulphureum, Fusarium toruloseum, Fusarium trichothecioides, Fusarium venenatum, Humicola insolens, Humicola lanuginosa, Monilia sitophila, Mucor miehei, Myceliophthora thermophila, Neurospora crassa, Penicillium expansum, Penicillium oxalicum, Penicillium purpurogenum, Phanerochaete chrysporum, Polyporus pinsitus, Polyporus versicolor, Rhizoctonia solani, Sclerotium rolfsii, Sporotrichum thermophile, Trichoderma citrinoviride, Trichoderma hamatum, Trichoderma harzianum, Trichoderma koningii, Trichoderma longibrachiatum, Trichoderma polysporum, Trichoderma reesei, Trichoderma saturnisporum*, or *Trichoderma viride* pectate lyase.

In a most preferred embodiment, the pectate lyase is a *Bacillus agaradherens* pectate lyase. In another most preferred embodiment, the pectate lyase is a *Bacillus licheniformis* pectate lyase.

The pectate lyase(s) may be obtained from the organism in question by any suitable technique, and in particular by use of recombinant DNA techniques known in the art (c.f. Sambrook, J. et aL, 1989, *Molecular Cloning, A Laboratory Manual*, Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA, or synthetic origin, or any mixture of these, and may be isolated or synthesized in accordance with methods known in the art. The enzyme may also be obtained from its naturally occurring source, such as a plant or organism, or relevant part thereof. Furthermore, the pectate lyase(s) may be obtained from commercial suppliers.

When a pectate lyase is added to dough intended for use in the preparation of baked products, it may exert a beta-elimination on the pectate present in the dough constituents. The pectate lyase(s) is used in an amount sufficient to provide the desired effect, i.e., the improved properties in question. Thus, the dosage of the pectate lyase(s) to be used in the methods of the present invention should be adapted to the nature and composition of the dough in question as well as to the nature of the pectate lyase(s) to be used.

The term "composition" is defined herein as a dough-improving and/or baked product-improving composition which, in addition to one or more pectate lyases, comprise one or more additional substances conventionally used in baking. The additional substance(s) may be other enzymes or chemical additives known in the art to be useful in dough preparation and/or baking.

The bread-improving and/or dough improving composition of the invention is generally included in the dough in an amount corresponding to 0.01–5%, in particular 0.1–3%. The pectate lyase(s) is typically added in an amount corresponding to 0.01–100 mg enzyme protein per kg of flour, preferably 0.1–25 mg enzyme protein per kg of flour, more preferably 0.1–10 mg enzyme protein per kg of flour, and most preferably 0.5–5 mg enzyme protein per kg of flour.

In terms of enzyme activity, the appropriate dosage of a given pectate lyase for exerting a desirable improvement of dough and/or baked products will depend on the enzyme in question. The skilled person may determine a suitable enzyme unit dosage on the basis of methods known in the art. For purposes of the present invention, pectate lyase activity is determined by the APSU activity assay or the β-transelimination activity assay as described in the Examples herein.

The pectate lyase(s) and/or additional enzymes to be used in the methods of the present invention may be in any form suitable for the use in question, e.g., in the form of a dry powder, agglomerated powder, or granulate, in particular a non-dusting granulate, a liquid, in particular a stabilized liquid, or a protected enzyme. Granulates and agglomerated powders may be prepared by conventional methods, e.g., by spraying the pectate lyase(s) onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy. The pectate lyase(s) and/or additional enzymes may be contained in slow-release formulations. Methods for preparing slow-release formulations are well known in the art. Liquid enzyme preparations may, for instance, be stabilized by adding nutritionally acceptable stabilizers such as a sugar, sugar alcohol, or another polyol, and/or lactic acid or another organic acid according to established methods.

For inclusion in pre-mixes or flour it is advantageous that the pectate lyase(s) is in the form of a dry product, e.g., a non-dusting granulate, whereas for inclusion together with a liquid it is advantageously in a liquid form.

One or more additional enzymes may also be incorporated into the dough. The additional enzyme(s) may be of any origin, including mammalian and plant, and preferably of microbial (bacterial, yeast, or fungal) origin and may be obtained by techniques conventionally used in the art.

In a preferred embodiment, the additional enzyme(s) may be an amylase, such as an alpha-amylase (useful for providing sugars fermentable by yeast and retarding staling); a beta-amylase; a cyclodextrin glucanotransferase; a peptidase, in particular, an exopeptidase (useful in flavour enhancement); a transglutaminase; a lipase (useful for the modification of lipids present in the dough or dough constituents so as to soften the dough); a phospholipase (useful for the modification of lipids present in the dough or dough constituents so as to soften the dough and improve gas retention in the dough); a cellulase; a hemicellulase, in particular a pentosanase such as xylanase (useful for the partial hydrolysis of pentosans which increases the extensibility of the dough); a protease (useful for gluten weakening in particular when using hard wheat flour); a protein disulfide isomerase, e.g., a protein disulfide isomerase as disclosed in WO 95/00636; a glycosyltransferase; a peroxidase (useful for improving the dough consistency); a laccase; or an oxidase, e.g., an aldose oxidase, a glucose oxidase, a pyranose oxidase, a lipoxygenase, or an L-amino acid oxidase (useful in improving dough consistency).

The xylanase is preferably of microbial origin, e.g., derived from a bacterium or fungus, such as a strain of Aspergillus, in particular of *Aspergillus aculeatus, Aspergillus niger* (cf. WO 91/19782), *Aspergillus awamori* (WO 91/18977), or *Aspergillus tubigensis* (WO 92/01793), from a strain of Trichoderma, e.g., *Trichoderma reesei*, or from a strain of Humicola, e.g., *Humicola insolens* (WO 92/17573, the contents of which is hereby incorporated by reference).

Commercially available amylases useful in the present invention are NOVAMYL™ (a *Bacillus stearothermophilus* maltogenic amylase, available from Novo Nordisk A/S, Denmark); FUNGAMYL® (an *Aspergillus oryzae* alpha-amylase, available from Novo Nordisk A/S, Denmark); and BAN™ (a *Bacillus licheniformis* alpha-amylase, available from Novo Nordisk A/S, Denmark). A commercially available amyloglucosidase useful in the present invention is AMG™ (an *Aspergillus niger* amyloglucosidase, available from Novo Nordisk A/S, Denmark). Other useful commercially available amylase products include GRINDAMYL™ A 1000 or A 5000 (available from Grindsted Products, Denmark) and AMYLASE H or AMYLASE P (available from Gist-Brocades, The Netherlands). A commercially available glucose oxidase useful in the present invention is GLUZYME™ (an *Aspergillus niger* glucose oxidase, available from Novo Nordisk A/S, Denmark). Commercially available proteases useful in the present invention are NEUTRASE™ (a *Bacillus amyloliquefaciens* endoprotease, available from Novo Nordisk A/S, Denmark) and GLUTENASE™ (available from Novo Nordisk A/S, Denmark). Commercially available pentosanases useful in the present invention are PENTOPAN™ (a *Humicola insolens* pentosanase, available from Novo Nordisk A/S, Denmark) and PENTOPAN™ MONO (a *Thermomyces lanuginosus* pentosanase, available from Novo Nordisk A/S, Denmark). A commercially available lipase useful in the present invention is NOVOZYM® 677 BG (a *Thermomyces lanuginosus* lipase, available from Novo Nordisk A/S, Denmark).

When one or more additional enzyme activities are to be added in accordance with the methods of the present invention, these activities may be added separately or together with the pectate lyase(s), optionally as constituent (s) of the bread-improving and/or dough-improving composition. The other enzyme activities may be any of the enzymes described above and may be dosed in accordance with established baking practices.

In addition to the above-mentioned additional enzymes, a pectate lyase may contain varying minor amounts of other enzymatic activities inherently produced by the producer organism in question.

In addition, or as an alternative, to additional enzyme components, a conventionally used baking agent may also be incorporated into the dough. The baking agent may include proteins, such as milk powder (to provide crust colour), gluten (to improve the gas retention power of weak flours), and soy (to provide additional nutrients and improve water binding); eggs such (either whole eggs, egg yolks or egg whites); fat such as granulated fat or shortening (to soften the dough and improve the texture of the bread); emulsifier(s) (to improve dough extensibility and, to some extent, the consistency of the resulting bread); oxidant(s), e.g., ascorbic acid, potassium bromate, potassium iodate, azodicarbon amide (ADA) or ammonium persulfate (to strengthen the gluten structure); amino acid(s), e.g., L-cysteine (to improve mixing properties); sugar; salt, e.g., sodium chloride, calcium acetate, sodium sulfate or calcium sulphate (to make the dough firmer); flour; and starch. Such components may also be added to the dough in accordance with the methods of the present invention.

Examples of suitable emulsifiers are monoglycerides or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, and lecithin.

The dough and/or baked product prepared by a method of the present invention may be based on wheat meal or flour, optionally in combination with other types of meal or flour such as corn meal, corn flour, rye meal, rye flour, oat meal, oat flour, soy meal, soy flour, sorghum meal, sorghum flour, potato meal, or potato flour.

The handling of the dough and/or baking may be performed in any suitable manner for the dough and/or baked product in question, typically including the steps of kneading the dough, subjecting the dough to one or more proofing treatments, and baking the product under suitable conditions, i.e., at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

From the above disclosure it will be apparent that the dough is generally a leavened dough or a dough to be subjected to leavening. The dough may be leavened in various ways such as by adding sodium bicarbonate or the like, or by adding a leaven (fermenting dough), but it is preferable that the dough is leavened by adding a suitable yeast culture, such as a culture of *Saccharomyces cerevisiae* (baker's yeast). Any of the commercially available *Saccharomyces cerevisiae* strains may be employed.

The present invention also relates to the use of a pectate lyase for the preparation of pasta dough, preferably prepared from durum flour or a flour of comparable quality. The dough may be prepared by use of conventional techniques and the pectate lyase(s) used in a similar dosage as that described above. When used in the preparation of pasta, the pectate lyase(s) results in a strengthening of the gluten structure, reduction in the dough stickiness, and increased dough strength.

The present invention also relates to methods for preparing a baked product, comprising baking a dough obtained by a method of the present invention to produce a baked product. The baking of the dough to produce a baked product may be performed using methods well known in the art.

The present invention also relates to compositions comprising an effective amount of one or more pectate lyases, for improving one or more properties of a dough and/or a baked product obtained from the dough, and a carrier and/or a baking ingredient. The compositions may further comprise one or more additional enzymes and/or one or more conventionally used baking agents. Such baking agents include, but are not limited to, protein, emulsifier, granulated fat, oxidant, amino acid, sugar, salt, flour, and starch as described earlier.

The present invention also relates to doughs and baked products, respectively, produced by the methods of the present invention.

The present invention further relates to a pre-mix, e.g., in the form of a flour composition, for dough and/or baked products made from dough, in which the pre-mix comprises one or more pectate lyases. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing a pectate lyase(s) or a bread-improving and/or dough-improving composition of the invention comprising a pectate lyase(s) with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise the pectate lyase(s). The baking additive preferably has a narrow particle size distribution with more than 95% (by weight) of the particles in the range from 25 to 500 μm.

The present invention is further described by the following examples that should not be construed as limiting the scope of the invention.

EXAMPLES

Materials and Methods

Preparation of White Bread (I)

The straight-dough bread-making method may be used according to AACC Method 10-10B (in Approved Methods of the American Association of Cereal Chemists, Ninth Edition, March 1995; AACC, St. Paul Minn., USA).

| Basic recipe | |
| --- | --- |
| Wheat flour | 100% |
| Salt | 1.5% |
| Yeast (fresh) | 5.3% |
| Sugar | 6.0% |
| Shortening | 3.0% |
| Water | optimum |

All percentages are by weight relative to the wheat flour.
Procedure
1. Dough mixing (Hobart mixer):
   The mixing time and speed should be determined by the skilled baker so as to obtain an optimum dough consistency under the testing conditions used.
2. 1st punch (e.g., 52 minutes after start)
3. 2nd punch (e.g., 25 minutes later)
4. Molding and panning (e.g., 13 minutes later)
5. Proofing to desired height (e.g, 33 minutes at 32° C., 82% RH)
5. Baking (e.g., at 215° C. for 24 minutes)

Preparation of White Bread (II)

The sponge-dough bread-making method may be used according to AACC Method 10-11 (in Approved Methods of the American Association of Cereal Chemists, Ninth Edition, March 1995; AACC, St. Paul Minn., USA).

| Basic recipe for Sponge | |
| --- | --- |
| Wheat flour | 60% |
| Yeast (compressed) | 36% |
| Yeast Food | 2% |
| Water | 36% |

All percentages are by weight relative to the wheat flour.
Procedure
1. Add water to compressed yeast
2. Add yeast food in dry form with flour
3. Mix sponge (Hobart A-120; Hobart Corp., Troy Ohio, USA):
   0.5 minute at $1^{st}$ speed
   1 minute at $2^{nd}$ speed
   The mixing time may be adjusted so as to obtain an optimum dough consistency under the testing conditions used.
4. Fermnent in a fermentation cabinet: 4 hours at 30° C., 85% RH

| Basic recipe for Dough | |
| --- | --- |
| Wheat flour | 40% |
| Water | 24% |
| Sugar | 5% |
| Shortening | 3% |
| Salt | 2% |

All percentages are by weight relative to the wheat flour.
Procedure
1. Add dough ingredients; begin mixer ($1^{st}$ speed)
2. Add sponge in three approximately equal portions at 15, 25, and 35 seconds mixing time; total mixing time: 1 minute
3. At $2^{nd}$ speed, mix to obtain an optimum dough consistency
4. Ferment in a fermentation cabinet: 30 minutes at 30° C., 85% RH
5. Intermediate proof: 12–15 minutes in fermentation cabinet
6. Mold and final proof at 35.5° C., 92% RH
7. Bake: 25 minutes at 218° C.

Evaluation of Staling Properties of Bread

The degree of staling is determined on bread, e.g., on day 1, 3, 7 and 9 after baking. Evaluation of staleness and texture can be done according to AACC method 74-09. The principles for determination of softness and elasticity of bread crumb are as follows:
1. A slice of bread is compressed with a constant speed in a texture analyser, measuring the force for compression in g.
2. The softness of the crumb is measured as the force at 25% compression.
3. The force at 40% compression (P2) and after keeping 40% compression constant for 30 seconds (P3) is measured. The ratio (P3/P2) is the elasticity of the crumb.

Preparation of White Layer Cake

The method may be used according to AACC Method 10-90 (in Approved Methods of the American Association of Cereal Chemists, Ninth Edition, March 1995; AACC, St. Paul Minn., USA).

| Basic recipe | |
|---|---|
| Flour | 100% |
| Sugar | 140% |
| Shortening | 50% |
| Nonfat Dry Milk | 12% |
| Dried Egg Whites | 9% |
| Salt | 3% |
| Baking Powder and Water | determined empirically |

All percentages are by weight relative to the flour.

Procedure
1. Combine all dry ingredients and sift well
2. Add shortening and 60% of water
3. Mix at low speed for 0.5 minute in Hobart C-100 mixer
4. Mix at medium speed for 4 minutes
5. Add 50% of remaining water
6. Mix at low speed for 0.5 minute, scrape down and mix at medium speed for 2 minutes
7. Add remaining water, mix at low speed for 0.5 minute, scrape down and mix at medium speed for 2 minutes
8. Scale batter into each of two greased pans
9. Bake at 375° C. or 350° C.

Evaluation of Cakes

Cakes should be graded for volume and texture on the same day as baked according to AACC Method 10-90.

The internal structure may be scored for the uniformity and size of cells as well as thickness of the walls; the grain; texture, such as moisture, tenderness and softness; crumb colour; and flavour.

Preparation of Cookies

Cookies may be prepared according to AACC Method 10-50D (in Approved Methods of the American Association of Cereal Chemists, Ninth Edition, March 1995; AACC, St. Paul Minn., USA).

| Basic recipe | |
|---|---|
| Flour | 225 g |
| Water | 16 g |
| Dextrose Solution | 33 g |
| Bicarbonate of Soda | 2.5 g |
| Salt | 2.1 g |
| Sugar | 130 g |
| Shortening | 64 g |

Procedure
1. Cream shortening, sugar, salt and soda on low speed 3 minutes using an electric mixer (e.g., Hobart C-100)
2. Add dextrose solution and distilled water
3. Mix at low speed for 1 minute
4. Mix at medium speed for 1 minute
5. Add all flour and mix at low speed for 2 minutes
6. Scrape dough from bowl and place six portions at well-spaced points on lightly greased cookie sheet
7. Flatten dough lightly
8. Cut dough with cookie cutter
9. Bake at 205° C. for 10 minutes Evaluation of Cookies Cookie width should be measured after cooling 30 minutes and can be done by the method according to AACC Method 10-50D.

The width of each of the six cookies is measured in mm, then rotated 90° and remeasured to obtain the average width (W). An average thickness (T) may be obtained by measuring the cookies stacked on top of one another, then restacked in a different order. The spread factor is the ratio of W/T. However, the most sensitive and reliable estimate is the width measurement, and in some cases, thickness. Because the spread factor is a ratio of 2 empirically determined parameters, different values of W and T can result in the same W/T.

Preparation of Biscuits

Biscuits may be prepared according to AACC Method 10-31B (in Approved Methods of the American Association of Cereal Chemists, Ninth Edition, March 1995; AACC, St. Paul Minn., USA).

| Basic recipe | |
|---|---|
| Flour | 228 g |
| Shortening | 40 g |
| Milk Solution[1] | 135 g |
| Bicarbonate of Soda[2] | 3.4 g |
| Salt[2] | 4.5 g |
| Monocalcium Phosphate[2] | 130 g |

[1]50 g milk powder in 450 ml water
[2]omit if self-rising flour is used; use 240 g of self-rising flour Procedure
1. Sift together flour and other dry ingredients (bicarbonate of soda, salt and monocalcium phosphate, if used)
2. Add shortening to flour mixture
3. Mix, using electric mixer (e.g., Hobart, Kitchen Aid or equivalent) with timer control, at speed 1 for 15 seconds
4. Mix at speed 1 for 3 minutes
5. Add milk solution and mix at speed 1 for 15 seconds
6. Roll out dough using floured rolling pin
7. Cut dough with floured cutter
8. Place 8 dough pieces 4 cm apart on ungreased baking sheet.
9. Bake at 232° C. for 10 minutes Evaluation of Biscuits Upon removal from oven, biscuits should be removed from the baking sheet and cooled for 30 minutes. Measurements of the eight biscuits can be made according to AACC Method 10-31B to obtain a total weight, a total diameter and a height at the top center of each biscuit.

Preparation of Pie Shells

Pie shells may be prepared according to AACC Method 10-60 (in Approved Methods of the American Association of Cereal Chemists, Ninth Edition, March 1995; AACC, St. Paul Minn., USA).

| Basic recipe | |
|---|---|
| Flour | 100% |
| Shortening | 60% |
| Salt | 3.5% |
| Water | 30–64% |

All percentages are by weight relative to the wheat flour, and all ingredients are at 10° C. before mixing.

Procedure
1. Sift flour twice
2. Add shortening to flour and cut for 5 minutes using electric mixer (e.g., Hobart, Kitchen Aid or equivalent) with timer control, on low speed 3. Dissolve salt in a portion of water
4. Add salt solution to flour-shortening mixture, together with additional water if necessary
5. Mix at low speed for 2 minutes
6. Store dough at 10° C. for 24 hours
   Empty shells
7. Scale, press dough into ball
8. Roll dough, fold and roll again
9. Fold and roll a third time
10. Lay dough sheet over an inverted pie tin
11. Trim dough and prick with fork
12. Let dry for 30 minutes and cover with a second pan pressed down firmly
13. Bake at 218° C. for 20–25 minutes, removing second pan after 10 minutes in the oven
    Filled pies
7. Scale and roll bottom crust as outlined above for empty pie shell
8. Press dough sheet into pie tin and fill with either artificial fruit acid filling (water, corn starch, sugar and citric acid crystals) or true fruit filling (cling peaches, sugar corn starch and water)
9. Scale and roll dough once for top crust
10. Place over filling, trim and cut center lightly
11. Press edge over wetted edge of bottom crust
12. Bake at 218° C. for about 30 minutes Evaluation of Pie Crusts Viscosity may be evaluated according to AACC Method 56-80. Other parameters of empty and filled pie shells may be measured according to AACC Method 10-60 24 hours and 12 or 16 hours after baking, respectively. Pie crusts may be evaluated empirically for whether they are baked through; the edges have shrunk from edge of pan; blisters have appeared; the texture is flaky; the mouth-feel is tender; whether they are crisp or soft; the colour; and if the fruit filling has penetrated the crust.

Testing of Doughs and Breads

According to the methods of the present invention, the effect of adding a pectate lyase may be tested in doughs and breads by using the following method:

| Recipe: | |
|---|---|
| Water | 60% |
| Wheat Flour | 100% |
| Yeast | 4% |
| Salt | 1.5% |
| Sugar | 1.5% |

The wheat flour is of the type Meneba 964.
Preparation of Breads
Procedure
1. Dough mixing (Spiral mixer)
   3 minutes at low speed
   8 minutes at high speed
   The mixing time may be adjusted by the skilled baker to obtain an optimum dough consistency under the testing conditions used.
2. 1st proof: 30° C.-80% RH, 20 minutes
3. Scaling and shaping
4. Final proof: 32° C.-80% RH, 40 minutes
5. Baking: 225° C., 20 minutes for rolls and 30 minutes for loaf Evaluation of Dough and Baked Products Dough and baked products made from the straight dough method described above may be evaluated as follows for loaf specific volume, dough stickiness, dough firmness, dough extensibility, dough elasticity, crumb structure, and gluten strength.

Loaf specific volume: The mean value of 4 loaves volume are measured using the traditional rape seed method. The specific volume is calculated as volume ml per g bread. The specific volume of the control (without enzyme) is defined as 100. The relative specific volume index is calculated as:

$$\text{Specific vol. index} = \frac{\text{specific vol. of 4 loaves}}{\text{spec. vol. of 4 control loaves}} \times 100$$

The dough stickiness, firmness, extensibility, elasticity and crumb structure may be evaluated relative to controls by the skilled test baker according to the following scale:

| Dough stickiness: | |
|---|---|
| almost liquid | 1 |
| too sticky | 2 |
| sticky | 3 |
| normal | 4 |
| dry | 5 |
| too dry | 6 |
| Crumb structure: | |
| very poor | 1 |
| poor | 2 |
| non-uniform | 3 |
| uniform/good | 4 |
| very good | 5 |
| Dough Firmness: | |
| extremely soft | 1 |
| too soft | 2 |
| soft/good | 3 |
| normal | 4 |
| firm | 5 |
| too firm | 6 |
| Dough Extensibility: | |
| too short | 1 |
| short | 2 |
| normal | 3 |
| good | 4 |
| long | 5 |
| too long | 6 |

Dough stability/Shock test: After the second proof a pan containing the dough is dropped from a height of 20 cm. The dough is baked and the volume of the resulting bread is determined.

Gluten Strengthening: The strengthening effect of a given dough conditioner on wheat flour dough or gluten dough may be measured by dynamic rheological measurements. These measurements are able to show the strength of a dough under oscillation. Both wheat flour dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ(Delta). An increase in the storage modulus G' and a decrease in the phase angle δ indicate a stronger and more elastic dough.

General Molecular Biology Methods

Unless otherwise mentioned, the DNA manipulations and transformations were performed using standard methods of molecular biology (Sambrook et al., 1989, *Molecular Cloning: A Laboratory Manual*, Cold Spring Harbor Laboratory, Cold Spring Harbor, N.Y.; Ausubel, F. M. et al. (eds.) *Current Protocols in Molecular Biology*. John Wiley and Sons, 1995; and Harwood, C. R., and Cutting, S. M. (eds.) *Molecular Biological Methods for Bacillus*. John Wiley and Sons, 1990).

Enzymes for DNA manipulations were used according to the specifications of the suppliers (e.g., restriction endonucleases, ligases, etc. were obtained from New England Biolabs, Inc.).

Example 1

Isolation of *Bacillus agaradherens* Genomic DNA and Construction of Genomic DNA Library

*Bacillus agaradherens* NCIMB 40482 (identical to *Bacillus agaradherens* DSM 8721) was propagated in liquid medium as described in WO 94/01532. After 16 hours incubation at 30° C. and 300 rpm, the cells were harvested, and genomic DNA was isolated according to the method of Pitcher et al., 1989, *Letters of Applied Microbiology* 8: 151–156.

The genomic DNA was partially digested with Sau 3A and size-fractionated by electrophoresis on a 0.7% agarose gel. Fragments between 2 and 7 kb in size were isolated onto DEAE-cellulose paper according to Dretzen et al., 1981, *Analytical Biochemistry* 112: 295–298. The isolated DNA fragments were then ligated to Bam HI digested pSJ1678, an *E. coli-Bacillus subtilis* shuttle vector (WO 94/19454).

*E. coli* SJ2 (Diderichsen et al., 1990, *Journal of Bacteriology* 172: 4315–4321) was electroporated with the ligated plasmid DNA using a Bio-Rad Gene Pulser™ electroporator according to the manufacturer's instructions. Transformed cells were plated onto LB agar plates containing 10 μg of chloramphenicol per ml and the plates were incubated for 18 hours at 37° C.

Example 2

Identification and Characterisation of Pectate Lyase Positive Clones

After incubation on plates the colonies were replica plated onto a set of LB agar plates supplemented with 6 μg of chloramphenicol per ml and then further incubated at 37° C. for approximately 20 hours. A polypectate overlayer in an appropriate buffer was poured onto the replica plates and incubated for approximately 20 hours at 65° C. Pectate lyase positive colonies were identified by the appearance of halos at positions where pectate lyase positive clones were present.

Cells from the pectate lyase positive colonies were spread for single colony isolation on agar, and a pectate lyase producing single colony was selected for each of the pectate lyase-producing colonies identified.

Plasmid DNA was extracted from the pectate lyase positive clones obtained as single colonies using a Qiagen Plasmid Prep Kit according to the manufacturer's instructions (Qiagen, Germany). Phenotypes were confirmed by retransformation of *E. coli* SJ2, and plasmids were characterized by restriction digests.

One positive clone was designated *E. coli* DSM 11788. *E. coli* DSM 11788 was deposited according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposit number DSM 11788.

Example 3

Expression in *Bacillus subtilis* of the Cloned *Bacillus agaradherens* Gene Encoding a Pectate Lyase A plasmid preparation of *E. coli* DSM 11788 (*E. coli* containing the cloned gene on pSJ1678) was used to transform *Bacillus subtilis* PL2306. *Bacillus subtilis* PL2306 is *Bacillus subtilis* DN1885 (Diderichsen, et al., 1990, *Journal of Bacteriology* 172: 4315–4321) with the genes aprE (Stahl and Ferrari, 1984, *Journal of Bacteriology* 158: 411–418) and nprE (Yang et al., 1984, *Journal of Bacteriology* 160: 16–21) disrupted. The strain was further disrupted in the transcriptional unit of the known *Bacillus subtilis* cellulase gene, resulting in cellulase negative cells. The disruption was performed essentially as described in A. L. Sonenshein, J. A. Hoch and Richard Losick, editors, 1993, *Bacillus subtilis and other Gram-Positive Bacteria*, American Society for Microbiology, p.618.

Competent *Bacillus subtilis* PL2306 cells were prepared and transformed according to the procedure described by Yasbin et al., 1975, *Journal of Bacteriology* 121: 296–304. The transformed *Bacillus subtilis* cells were plated on LB agar plates containing 6 μg of chloramphenicol per ml, 0.4% glucose, and 10 mM $KH_2PO_4$, and incubated at 37° C. for 18 hours. Pectate lyase positive colonies were identified as described earlier for the *E. coli* clones.

The positive transformants were each inoculated into 10 ml of TY medium (Ausubel et al., eds., *Current Protocols in Molecular Biology*, John Wiley and Sons, 1995) containing 6 μg of chloramphenicol per ml. After 1 day of incubation at 37° C. and 250 rpm, samples of 50 μl were removed and centrifuged to remove the cells. The supernatants were added to wells punched in LB agar plates containing 0.7% sodium polypectate (Sigma Chemical Co., St. Louis, Mo.).

After 16 hours of incubation at 37° C., plates were soaked in 1 M $CaCl_2$ for 5 to 30 minutes. Distinct cloudy halos appeared where supernatant contained pectate lyase activity. One such *Bacillus subtilis* clone was designated *Bacillus subtilis* MB464.

Example 4

Purification and Characterization of Pectate Lyase Cloned from *Bacillus agaradherens*

The *Bacillus subtilis* MB464 clone described in Example 3 was inoculated in 100 ml of TY medium supplemented with 6 μg of chloramphenicol per ml. After overnight incubation at 37° C. and 250 rpm, 1 ml of the culture was used as an inoculum in 1 liter shake flasks each containing 100 ml of Complex Growth Medium (U.S. Pat. No. 5,371,198). The cultures were incubated at 37° C. and 250 rpm for 4 days.

The fermentation medium was adjusted to pH 7.5 with NaOH and flocculated using cationic flocculation agent C521 (10% solution) and 0.1% solution of anionic agent A130: To 6500 ml of fermentation medium was added 306 ml of C521 (10%) simultaneous with 608 ml of A130 under stirring at room temperature. The flocculated material was separated by centrifugation using a Sorval RC 3B centrifuge at 10,000 rpm for 30 minutes. The supernatant was clarified using Whatman glass filter number F. A volume of 7200 ml of clear solution was obtained.

The filtered solution was assayed for APSU activity which is a viscosity measurement using the substrate polygalacturonic acid with no added calcium. The substrate 5% polygalacturonic acid sodium salt (Sigma P-1879) was solubilized in 0.1 M glycine pH 10 buffer. A 4 ml volume of the substrate was preincubated for 5 minutes at 40° C. The enzyme was added in a volume of 250 μl to the substrate solution, mixed for 10 seconds on a mixer at maximum speed, and incubated for 20 minutes at 40° C. The viscosity was measured using a MIVI 600 from Sofraser, 45700 Villemandeur, France. The viscosity was measured as mV after 10 seconds. For a standard curve, the determination was performed in duplicate with a dilution of enzyme concentration in the range of 5 APSU/ml to above 100 APSU/ml with minimum of 4 concentrations between 10 and 60 APSU per ml.

For calculation of APSU units, a enzyme standard dilution as described above was used for obtaining a standard curve. The GrafPad Prism program, using a non linear fit with a one phase exponential decay with a plateau, was used for calculations. The plateau plus span is the mV obtained without enzyme. The plateau is the mV of more than 100 APSU and the half reduction of viscosity in both examples was found to be 12 APSU units with a standard error of 1.5 APSU. The filtered solution was determined to contain 324,000 APSU units.

The solution was concentrated into 2 portions of 500 ml and 840 ml using filtron ultrafiltration with a molecular weight cut-off of 10 kDa.

The pH was adjusted to 5.3 using acetic acid, and the concentrate was applied to a 200 ml S-Sepharose column equilibrated with 50 mM sodium acetate pH 5.3 buffer. The *Bacillus agaradherens* pectate lyase was eluted using a 2 liter linear gradient with 0.5 M NaCl as final concentration. The *Bacillus subtilis* pectate lyase will also bind to Sepharose at this pH but it has a higher isoelectric point (7.6 versus 6.0). The cloned *Bacillus agaradherens* pectate lyase eluted first. The fractions were analyzed for APSU units and for reaction with antiserum raised against *Bacillus subtilis* pectate lyase (denoted MB331).

The *Bacillus agaradherens* pectate lyase was concentrated using an Amicon ultrafiltration cell with a GR61 membrane with a molecular weight cut-off of 20 kDa. A total of 105 ml containing 90,000 APSU units was obtained. This sample was free of protease and the *Bacillus subtilis* pectate lyase activity which was determined using antiserum raised against *Bacillus subtilis* (MB331).

The pectate lyase enzyme was observed by SDS-PAGE as a band with a molecular weight of 36 kDa. After electroblotting of this band the N-terminal was determined to be:
Ser-Asn-Gly-Pro-Gln-Gly-Tyr-Ala-Ser-Met-Asn-Gly-Gly-Thr (SEQ ID NO:2)

This N-terminal sequence was in agreement with the amino acid sequence shown in SEQ ID NO:2 deduced from the DNA sequence shown in SEQ ID NO:1 with a 33 amino acid pro sequence. The calculated molecular weight from the deduced sequence was 36 kDa and the calculated isoelectric point was 6. The molar extinction coefficient at 280 nm was 48,930.

The β-transelimination activity of the pectate lyase was determined at different pH values by steady state kinetics at 40° C. as described below. For determination of β-transelimination activity, the increase in absorbance at 235 nm was measured using the substrate 0.1% polygalacturonic acid sodium salt (Sigma P-1879, Sigma Chemical Co., St. Louis, Mo.) solubilised in 0.1 M glycine pH 10 buffer. The steady state kinetics were performed using a 0.5 ml cuvette with a 1 cm light path on a HP diode array spectrophotometer in a temperature controlled cuvette holder with continuous measurement of the absorbency at 235 nm. For steady state, a linear increase for at least 200 seconds was used for calculation of the rate which was converted to μmole of product formed per minute.

For calculation of the catalytic rate, an increase of 5.2 absorbency at 235 units per minute corresponded to formation of 1 μmole of unsaturated product (Nasuna and Starr, 1966, *Journal of Biological Chemistry* 241: 5298–5306; and Bartling et al., 1995, *Microbiology* 141: 873–881). The relative rate was calculated as percentage of the optimum activity.

The following results were obtained for % relative activity vs. pH:

| pH | % relative activity |
|---|---|
| 6.5 | 0 |
| 7 | 5 |
| 7.5 | 8 |
| 8 | 21 |
| 8.5 | 32 |
| 9 | 38 |
| 9.5 | 39 |
| 10 | 52 |
| 10.5 | 47 |
| 11 | 100 |
| 11.2 | 66 |
| 11.5 | 3 |

Correspondingly, the following results were obtained for % relative activity at different temperatures (at pH 10):

| temp. ° C. | % relative activity |
|---|---|
| 40 | 69 |
| 50 | 100 |
| 55 | 97 |
| 60 | 68 |
| 65 | 71 |

Example 5
Construction of pMOL944 pMOL944 is a pUB110 derivative containing elements making the plasmid propagatable in *Bacillus subtilis*. The plasmid also contains a kanamycin resistance gene and a strong promoter and signal peptide cloned from the amyL gene of *Bacillus licheniformis* ATCC14580. The signal peptide contains a Sac II site making it convenient to clone a DNA fragment encoding the mature part of a protein in-fusion with the signal peptide. This results in the expression of a Pre-protein which is directed towards the exterior of the cell.

pUB110 (McKenzie et al., 1986, *Plasmid* 15: 93–103) was digested with Nci I. A PCR fragment amplified from the amyL promoter encoded on the plasmid pDN1981 (Jørgensen et al., 1990, *Gene*, 96: 37–41) was digested with Nci I and inserted in the Nci I digested pUB110 to yield pSJ2624. The two PCR primers used have the following sequences:
LWN5494:
5'-GTCGCCGGGGCGGCCGCTATCAATTGGTAACTGT ATCTCAGC-3' (SEQ ID NO:3)
LWN5495:
5'-GTCGCCCGGGAGCTCTGATCAGGTACCAAGCTTG TCGACCTGCAGAATGAGGC AGCAAGAAGAT-3' (SEQ ID NO:4)
The primer #LWN5494 inserted a Not I site in the plasmid.

pSJ2624 was then digested with Sac I and Not I. The PCR fragment containing the amyL promoter was digested with Sac I and Not I. This DNA fragment was inserted in Sac I-Not I digested pSJ2624 to yield pSJ2670.

This cloning replaced the first amyL promoter cloning with the same promoter but in the opposite direction. The two primers used for PCR amplification were:

LWN5938:
5'-GTCGGCGGCCGCTGATCACGTACCAAGCTTGTCG ACCTGCAGAATGAGGCAG CAAGAAGAT-3' (SEQ ID NO:5)
LWN5939:
5'-GTCGGAGCTCTATCAATTGGTAACTGTATCTCAG C-3' (SEQ ID NO:6)

pSJ2670 was digested with Pst I and Bcl I and a PCR fragment amplified from a cloned DNA sequence encoding the alkaline amylase SP722 was digested with Pst I and Bcl I and inserted to yield pMOL944. The two primers used for PCR amplification were:
LWN7864:
5'-AACAGCTGATCACGACTGATCTTTTAGCTTGGCA C-3' (SEQ ID NO:7)
LWN7901:
5'-AACTGCAGCCGCGGCACATCATAATGGGACAAAT GGG-3' (SEQ ID NO:8)

The primer #LWN7901 inserted a Sac II site in the plasmid.

Example 6
Isolation of *Bacillus licheniformis* Genomic DNA and PCR Amplification of Pectate Lyase Gene

*Bacillus licheniformis* ATCC 14580 (identical to *Bacillus licheniformis* DSM 8721) was propagated in liquid medium 3 as specified by ATCC (American Type Culture Collection, USA). After 18 hours incubation at 37° C. and 300 rpm, the cells were harvested, and genomic DNA was isolated according to the method of Pitcher et al., 1989, supra.

The pectate lyase encoding DNA sequence was PCR amplified using the PCR primer set consisting of the following two oligonucleotides:
Pecl.B.lich.upper.Sac II:
5'-CTAACTGCAG CCGCGGCAGCTTCTGCCTTAAACTCGGGC-3' (SEQ ID NO:9)
Pecl.B.lich.lower.Not I:
5'-GCGTTGAGACGC GCGGCCGCTGAATGCCCCGGACGTTTCACC-3' (SEQ ID NO:10)
Restriction sites Sac II and Not II are underlined.

The chromosomal DNA isolated from *Bacillus licheniformis* ATCC 14580 was used as template in the PCR reaction using Amplitaq DNA Polymerase (Perkin Elmer) according to manufacturer's instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA), and 100 pmol of each primer described above.

The PCR reactions were performed using a DNA thermal cycler (Landgraf, Germany) programmed for 1 cycle at 94° C. for 1 minute; 30 cycles of denaturation each at 94° C. for 30 seconds; annealing at 60° C. for 1 minute; and extension at 72° C. for 2 minutes. Five µl aliquots of the amplification products were analysed by electrophoresis in 0.7% agarose gels (NuSieve, FMC). The appearance of a DNA fragment of 1.0 kb indicated proper amplification of the gene segment.

The PCR fragment was cloned into pSJ1678 and transformed into *E. coli* using the same procedures described in Examples 1 and 2 to produce a positive clone designated *E. coli* DSM 11789. *E. coli* DSM 11789 was deposited according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Sep. 25, 1997 under the deposit number DSM 11789.

Example 7
Subcloning of *Bacillus licheniformis* Pectate Lyase Gene

Aliquots of 45 µl of the PCR products generated as described in Example 6 were purified using a QIAquick PCR Purification Kit (Qiagen, USA) according to the manufacturer's instructions. The purified DNA was eluted in 50 µl of 10 mM Tris-HCl pH 8.5. A 5 µg sample of pMOL944 and 25 µl of the purified PCR fragment were digested with Sac II and Not I and electrophoresed on 0.8% low gelling temperature agarose (SeaPlaque GTG, FMC) gels. The relevant fragments were excised from the gels and purified using a QIAquick Gel Extraction Kit (Qiagen, USA) according to the manufacturer's instructions. The isolated PCR DNA fragment was then ligated to the Sac II-Not I digested and purified pMOL944. The ligation was performed overnight at 16° C. using 0.5 µg of each DNA fragment, 1 U of T4 DNA ligase, and T4 ligase buffer (Boehringer Mannheim, Germany).

Competent *Bacillus subtilis* PL2306 cells were transformed with the ligation mixture. The transformed cells were then plated onto LBPG plates (LB agar supplemented with 0.5% Glucose and 0.05 M potassium phosphate, pH 7.0) supplemented with 10 µg of kanamycin per ml. After 18 hours incubation at 37° C., several clones were restreaked on fresh agar plates and also grown in liquid TY cultures supplemented with 10 µg of kanamycin per ml and incubated overnight at 37° C. A 1 ml volume of the overnight cells was used to isolate plasmid using the Qiaprep Spin Plasmid Miniprep Kit (Qiagen, USA) according to the manufacturer's recommendations for *Bacillus subtilis* plasmid preparations. This plasmid DNA was used as template for DNA sequencing.

One clone containing the pectate lyase gene was isolated and designated *Bacillus subtilis* MB541.

The DNA corresponding to the mature part of the pectate lyase was characterised by DNA sequencing by primer-walking, using the Taq deoxy terminal cycle sequencing kit (Perkin-Elmer, USA), fluorescent labelled terminators and appropriate oligonucleotides as primers.

Analysis of the sequence data was performed according to Devereux et al., 1984, *Nucleic Acids Research* 12: 387–395. The cloned DNA sequence represented by SEQ ID NO:11 was expressed in *Bacillus subtilis* and the protein that appeared in the supernatant corresponded to the mature protein represented by amino acids 1–341 of SEQ ID NO:12.

Example 8
Purification and Characterization of Pectate Lyase Cloned from *Bacillus licheniformis*

*Bacillus subtilis* MB541 was grown in 25×200 ml of BPX medium (WO 91/09129) with 10 µg of kanamycin per ml in two 500 ml baffled shake flasks for 5 days at 37° C. and 300 rpm, whereby 3500 ml of culture broth was obtained. The pH was adjusted to 5.0 using acetic acid and 100 ml of cationic agent (C521) and 200 ml of anionic agent (A130), which were added during agitation for flocculation. The flocculated material was separated by centrifugation using a Sorval RC 3B centrifuge at 10,000 rpm for 30 minutes at 6° C. The resulting supernatant contained 370 APSU per ml in a total volume of 3600 ml.

The supernatant was clarified using Whatman glass filters GF/D and C, concentrated on a filtron with a molecular weight cut-off of 10 kDa to 2000 ml, and adjusted to pH 8.5.

A total of 50 gram of DEAE A-50 Sephadex (Pharmacia) was swelled in 2000 ml of 50 mM Tris pH 8.5 buffer. Excess buffer was discarded and the clear concentrated enzyme solution was mixed with the slurry for 15 minutes. The enzyme was separated from the ion-exchange material by suction on a Buchner funnel. The resulting filtrate solution was concentrated on a filtron with a molecular weight cut-off of 10 kDa to 700 ml. The 700 ml solution was then formulated using 350 gram of sorbitol yielding a product MB 541-2 batch 9751.

For obtaining a highly purified pectate lyase, a final step using S-Sepharose cation-exchange chromatography was carried out. A 50 ml volume containing 950 APSU per ml was adjusted to pH 5.0 using acetic acid and loaded onto a 50 ml column containing S-Sepharose (Pharmacia) equilibrated with 50 mM sodium acetate pH 5.0 buffer. The bound pectate lyase was eluted using a gradient of 0 to 0.5 M sodium chloride.

The pure enzyme had a single band by SDS-PAGE of 35 kDa with an isolectric point of 9.3. The protein concentration was determined using a molar extinction coefficient of 57750 (based on the amino acid composition deducted from the sequence). Using the assay of detection where the formation of a double bound is measured at 235 nm, the following data were obtained:

1. (conditions: pH 10; glycine buffer; no calcium; polygalacturonic acid Sigma P-1879 as substrate): 1 µmole per minute per mg.

2. (conditions: pH 10; glycine buffer; no calcium; DE 35, 35% esterified pectin, as substrate): 4 µmole per minute per mg.

The temperature optimum was determined to be 65° C.

Rabbit antiserum was raised against the purified pectate lyase and isolated using standard methods (0.1 mg protein per rabbit per immunization).

Example 9

Purification and Characterisation of Pectate Lyase from *Bacillus licheniformis*

A pectate lyase from *Bacillus licheniformis* was purified from a production concentrate of the commercially available enzyme product Pulpzyme™ HC (from Novo Nordisk A/S, DK2880 Bagsvaerd, Denmark) which is a fermentation of *Bacillus licheniformis* for production of a xylanase.

A total of 800 ml of the concentrate containing 14400 APSU units was applied to a 800 ml S-Sepharose column equilibrated with 25 mM sodium acetate pH 5.0 buffer. The pectate lyase bound to the column was eluted using a linear gradient of 10 liters ending with 0.5 M sodium chloride in the same buffer. The fractions were assayed for β-transelimination activity at 235 nm using the method described in Example 4 and the active fractions were pooled. A total of 11000 APSU units was recovered and concentrated using an Amicon ultrafiltration cell equipped with a GR61 membrane with a molecular weight cut-off of 20 kDa. This partly purified fraction was used for characterization.

SDS-PAGE indicated that it was 25% pure based on a molecular weight of 34 kDa which was indicated by the following experiment. A small amount was purified further for determination of the specific activity and molecular weight. It was passed over a Superdex 200 column in buffer containing 0.1 M sodium acetate. The fractions were assayed for activity at 235 nm. The active fraction was pooled and concentrated again and then passed over a Superdex 75 column. The fraction with the highest activity had a specific activity of 120 APSU (pH 10) per mg protein and a molecular weight of 34 kDa by SDS-PAGE.

The β-transelimination activity (using the lyase assay at 235 nm as described in Example 4) at different pH values was determined using steady state kinetics at 40° C. The relative rate was calculated as percentage of the optimum activity. The following results were obtained for % relative activity vs. pH:

| pH | % activity |
|---|---|
| 6.5 | 1 |
| 7 | 5 |
| 7.5 | 4 |
| 8 | 4 |
| 8.5 | 4 |
| 9 | 6 |
| 9.5 | 23 |
| 10 | 100 |
| 10.5 | n.d. |
| 11 | 52 |
| 11.2 | 0 |

Correspondingly, the following results were obtained for % relative activity at different temperatures (at pH 10):

| temp. ° C. | % activity |
|---|---|
| 40 | 65 |
| 50 | 87 |
| 55 | 87 |
| 60 | 100 |
| 65 | 90 |

Example 10

Baking with Pectate Lyases

The *Bacillus lichenformis* and *Bacillus agaradherans* pectate lyases expressed in *Bacillus subtilis* as described in Examples 4 and 8, respectively, were evaluated in baking. Both enzymes were dosed at 30 mg/kg flour level using the "Basic White" bread recipe described earlier using a Welbilt bread machine Model ABM6000 (Welbilt, Great Neck, N.Y.). The *Bacillus lichenformis* pectate lyase increased the loaf volume by ~5% while the *Bacillus agaradherans* pectate lyase showed no detectable effect.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended any of claims. In the case of conflict, the present disclosure including definitions will control.

Various references are cited herein, the disclosures of which are incorporated by reference in their entireties.

What is claimed is:

1. A method for preparing a dough, comprising incorporating into the dough an effective amount of a pectate lyase, wherein the effective amount of the pectate lyase is about 0.01 mg to about 100 mg per kilogram of the dough.

2. The method of claim 1, wherein the pectate lyase improves one or more properties of the dough, a baked product obtained from the dough, or the dough and the baked product obtained from the dough.

3. The method of claim 2, wherein the one or more properties are selected from the group consisting of increased strength of the dough, increased stability of the dough, reduced stickiness of the dough, improved machinability of the dough, increased volume of the baked product, improved crumb structure of the baked product, improved softness of the baked product, improved flavor of the baked product, and improved antistaling of the baked product.

4. The method of claim 1, wherein the pectate lyase is obtained from a microbial source.

5. The method of claim 1, wherein the effective amount of the pectate lyase is about 0.1 mg to about 25 mg per kilogram of the dough.

6. The method of claim 4, wherein the effective amount of the pectate lyase is about 0.5 mg to about 5 mg per kilogram of the dough.

7. The method of claim 6, wherein the effective amount of the pectate lyase is about 1 mg to about 5 mg per kilogram of the dough.

8. The method of claim 1, wherein the dough is obtained from one or more ingredients selected from the group consisting of wheat meal, wheat flour, corn meal, corn flour, durum flour, rye meal, rye flour, oat meal, oat flour, soy meal, soy flour, sorghum meal, sorghum flour, potato meal, and potato flour.

9. The method of claim 1, wherein the dough is fresh or frozen.

10. The method of claim 2, wherein the baked product is selected from the group consisting of a bread, a roll, a French baguette-type bread, a pasta, a pita bread, a tortilla, a taco, a cake, a pancake, a biscuit, a cookie, a pie crust, steamed bread, and a crisp bread.

11. The method of claim 1, further comprising incorporating one or more additional enzymes selected from the group consisting of an amylase, cellulase, cyclodextrin glucanotransferase, glycosyltransferase, hemicellulase, laccase, lipase, oxidase, pentosanase, peptidase, peroxidase, phospholipase, protease, protein disulfide isomerase, and transglutaminase.

12. The method of claim 10 wherein the amylase is a *Bacillus stearothermophilus* maltogenic amylase.

13. The method of claim 1, further comprising incorporating one or more additives selected from the group consisting of a protein, emulsifier, granulated fat, oxidant, amino acid, sugar, salt, flour, and starch.

14. A method for preparing a baked product, comprising baking a dough obtained by the method of claim 1 to produce a baked product.

15. A composition comprising a baking agent and an effective amount of a pectate lyase for improving one or more properties of a dough or a baked product obtained from the dough, wherein the effective amount of the pectate lyase is about 0.01 mg to about 100 mg per kilogram of dough.

16. The composition of claim 15, further comprising one or more additives selected from the group consisting of a protein, emulsifier, granulated fat, oxidant, amino acid, sugar, salt, flour, and starch.

17. The composition of claim 15, wherein the pectate lyase improves one or more properties of the dough, a baked product obtained from the dough, or the dough and the baked product obtained from the dough.

18. The composition of claim 15, wherein the one or more improved properties are selected from the group consisting of increased strength of the dough, increased stability of the dough, reduced stickiness of the dough, improved machinability of the dough, increased volume of the baked product, improved crumb structure of the baked product, improved softness of the baked product, improved flavor of the baked product, and improved antistaling of the baked product.

19. The composition of claim 15, wherein the composition further comprises one or more additional enzymes selected from the group consisting of an amylase, a cellulase, a cyclodextrin glucanotransferase, a glycosyltransferase, a hemicellulase, a laccase, a lipase, an oxidase, a pentosanase, a peptidase, a peroxidase, a phospholipase, a protease, a protein disulfide isomerase, and a transglutaminase.

20. The composition of claim 15, wherein the composition further comprises one or more additives selected from the group consisting of a protein, emulsifier, granulated fat, oxidant, amino acid, sugar, salt, flour, and starch.

21. A dough obtained from the method of claim 1.

22. A baked product produced by the method of claim 13.

23. A pre-mix for a dough comprising an effective amount of a pectate lyase for improving one or more properties of a dough and/or a baked product obtained from the dough and a baking agent, wherein the effective amount of the pectate lyase is about 0.01 mg to about 100 mg per kilogram of dough.

24. A baking additive in the form of a granulate or agglomerated powder, which comprises a baking agent and an effective amount of a pectate lyase for improving one or more properties of a dough and/or a baked product obtained from the dough, wherein the effective amount of the pectate lyase is about 0.01 mg to about 100 mg per kilogram of dough, and more than 95% by weight of the baking additive has a particle size between about 25 and about 500 µm.

\* \* \* \* \*